(12) United States Patent
Cristini

(10) Patent No.: US 8,368,407 B2
(45) Date of Patent: Feb. 5, 2013

(54) DEVICE FOR MEASURING THE THICKNESS OF A LAYER OF MATERIAL

(75) Inventor: Giovanni Cristini, Bergamo (IT)

(73) Assignee: S.A. Giuseppe Cristini S.p.A., Milan (IT)

( * ) Notice: Subject to any disclaimer, the term of this patent is extended or adjusted under 35 U.S.C. 154(b) by 376 days.

(21) Appl. No.: 12/665,891

(22) PCT Filed: Jun. 20, 2008

(86) PCT No.: PCT/IB2008/001615
§ 371 (c)(1),
(2), (4) Date: Apr. 28, 2010

(87) PCT Pub. No.: WO2008/155645
PCT Pub. Date: Dec. 24, 2008

(65) Prior Publication Data
US 2010/0207642 A1   Aug. 19, 2010

(30) Foreign Application Priority Data

Jun. 21, 2007 (IT) .................................. MI07A1250

(51) Int. Cl.
*G01R 27/04* (2006.01)
*G01R 27/22* (2006.01)

(52) U.S. Cl. ........................................ 324/644; 324/637
(58) Field of Classification Search ........................ None
See application file for complete search history.

(56) References Cited

U.S. PATENT DOCUMENTS

| | | | | |
|---|---|---|---|---|
| 2,871,770 A | * | 2/1959 | Jackson | 162/13 |
| 3,522,527 A | * | 8/1970 | Williams et al. | 324/636 |
| 5,934,997 A | * | 8/1999 | Nelson et al. | 460/7 |
| 7,151,380 B2 | * | 12/2006 | Typpo et al. | 324/643 |
| 7,423,435 B2 | * | 9/2008 | Sawamoto et al. | 324/644 |
| 7,705,610 B2 | * | 4/2010 | Bray et al. | 324/644 |
| 2004/0083950 A1 | * | 5/2004 | Nissinen et al. | 118/58 |

FOREIGN PATENT DOCUMENTS

| | | |
|---|---|---|
| CN | 1880947 | 12/2006 |
| EP | 1624298 A2 | 2/2006 |
| EP | 1734361 A1 | 12/2006 |
| WO | WO-0009994 A1 | 2/2000 |

OTHER PUBLICATIONS

Chinese Office Action in CN 200880102254.7.
International Search Report in PCT/IB2008/001615 dated Dec. 5, 2008.

* cited by examiner

*Primary Examiner* — Vinh Nguyen
(74) *Attorney, Agent, or Firm* — Marshall, Gerstein & Borun LLP

(57) ABSTRACT

A device for measuring the thickness of a layer of material, the device including a reading head and control unit connected to the reading head. The reading head includes a microwave planar type sensor and an A/D converter connected to the microwave sensor and arranged in proximity of the microwave sensor.

12 Claims, 5 Drawing Sheets

DEVICE FOR MEASURING THE THICKNESS OF A LAYER OF MATERIAL

CROSS-REFERENCE TO RELATED APPLICATIONS

This is the U.S. national phase of International Application No. PCT/IB2008/001615, filed Jun. 20, 2008, which claims the benefit of Italian Patent Application No. MI2007A001250, filed Jun. 21, 2007.

TECHNICAL FIELD

The present invention refers to a device for measuring the thickness of a layer of material. In particular, the present invention refers to a device for measuring the thickness of a cellulosic pulp in a paper making machine.

BACKGROUND ART

As is known, in a paper making machine, a layer of cellulosic pulp, composed of approximately 3% fibre and mineral additives and approximately 97% water, is fed along a paper production line.

This production line goes through, in sequence, a cellulosic pulp formation and drainage section, a pressing section which produces a sheet of paper and a paper sheet drying section.

A first portion of the production line, which goes through the formation and drainage section, defines a drainage path, along which the cellulosic pulp is fed while supported by a fabric, that rotates in a loop, generally known as a "forming fabric". Underneath the forming fabric, and in contact with the reverse side of the same fabric, is arranged, at a predetermined distance from one another, a number of blades (generally known as "foils") and a number of suction units. The blades and the suction units are apt to remove the water contained between the fibres of the cellulosic pulp and which passes through the forming fabric as it advances. In particular, the blades remove the water that drains from the forming fabric by mechanical removal, whereas the suction units eliminate the water by the application of a vacuum.

A highly efficient formation and drainage section reduces the cost of pressing and drying operations carried out downstream of the formation and drainage section.

Portable devices are commercially available which monitor the efficiency of the formation and drainage station, by generally measuring the thickness of the cellulosic pulp layer or the amount of water contained in the cellulosic pulp.

Such devices generally include a rod on which a reading head is mounted and provided with a sensor, which is manually positioned in contact with the lower surface of the fabric between one suction unit and another, so as to measure the thickness of the cellulosic pulp layer positioned above the forming fabric.

Such devices employ various types of sensors, for example sensors that utilize GBS (Gamma Back Scattering) technology to measure the consistency of the material they contact. Such technology is accurate, but requires a radioactive source inside the reading head which makes it expensive and of no practical use due to the drawbacks of radioactivity. Other sensors utilize ultrasound and even if they are less expensive than the previous type, are difficult to use and are characterized by poor accuracy, especially in the environment of paper making machines.

Portable devices that utilize microwave sensors are also known, which estimate the quantity of water contained in the material by measuring the frequency response of the material. Such sensors are equipped with a resonance chamber made of very expensive metal-based alloy materials, since it is necessary to minimize the thermal expansion or contraction effects. In such sensors, in fact, the thermal expansion or contraction causes a shift in the resonance frequency which affects the response and, therefore, the accuracy of the measurement of the sensor. In addition, the field of microwaves output by sensors of this type has a poorly defined shape and a limited penetration capacity inside the layer of material. Hence such sensors cannot be used with very thick layers of material. Finally, the resonance chamber of such microwave sensors have minimum dimensions that do not allow the sensor to be integrated inside the blades of the formation and drainage section.

DISCLOSURE OF INVENTION

The object of the present invention is to provide a device for measuring the thickness of a layer of material containing water and, in particular, the thickness of a cellulosic pulp layer for paper making, which is free from the aforesaid drawbacks and, at the same time, is easy and cheap to produce.

In accordance with such object, the present invention concerns a device for measuring the thickness of a layer of material as claimed in claim 1.

An additional object of the present invention is to provide a paper making machine, including the device for measuring the thickness of a layer of material with the purpose of monitoring the drainage stage in the formation and drainage section of the machine.

In accordance with such further object, the present invention concerns a paper making machine as claimed in claim 7.

BRIEF DESCRIPTION OF THE DRAWINGS

Additional features and advantages of the present invention will appear clear from the following non-limiting description of an embodiment, with reference to the figures of the enclosed drawings, in which.

BEST MODE FOR CARRYING OUT THE INVENTION

Figure 1:
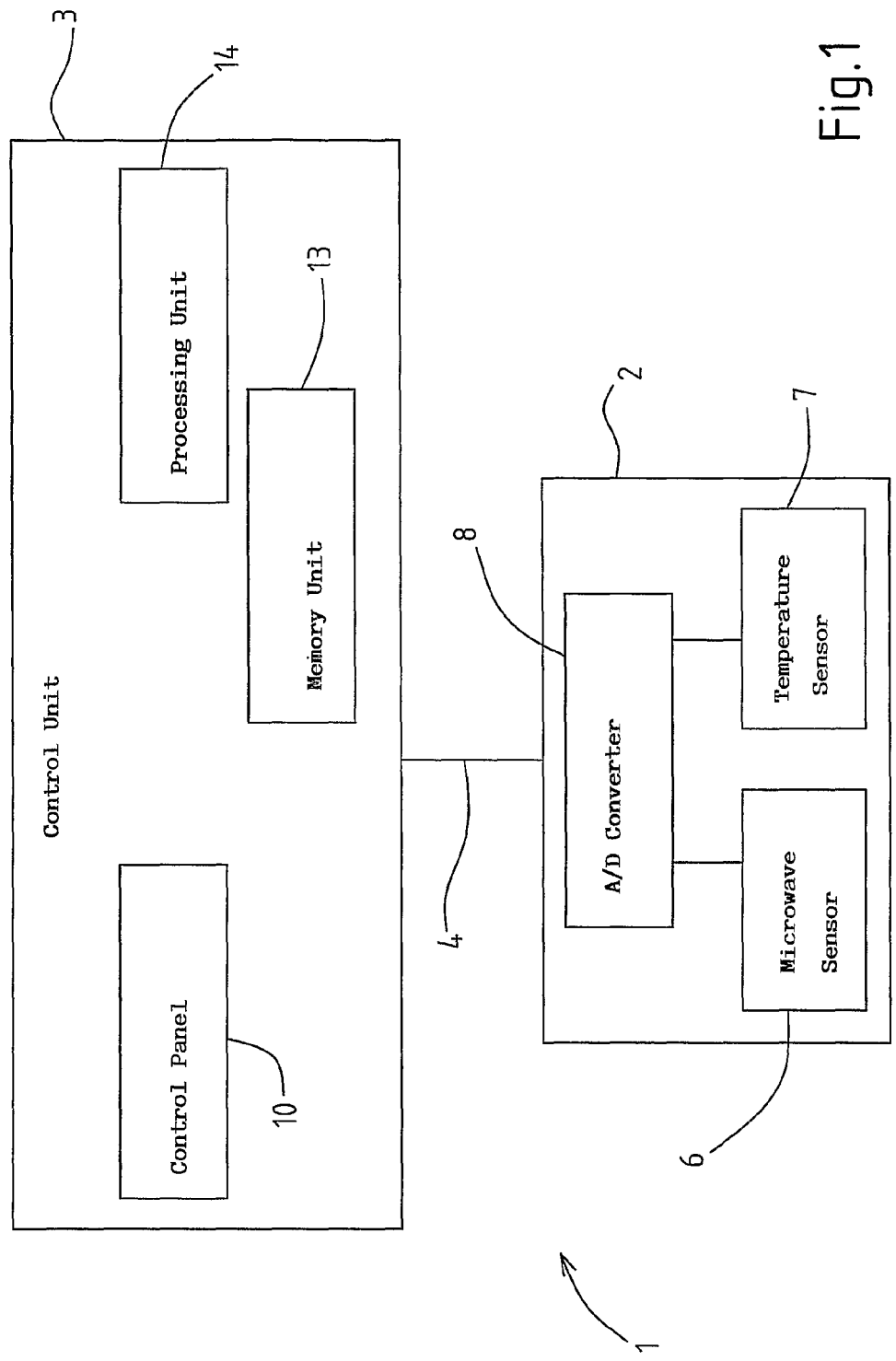
FIG. 1 shows a simplified block diagram of the device for measuring a layer of material according to the present invention.

In FIG. 1, reference number 1 represents a device for measuring the thickness of a layer of material according to the present invention. The device 1 includes a reading head 2 and a control unit 3, which are connected together, for example by means of a connection cable 4.

The reading head 2 includes a microwave sensor 6, a temperature sensor 7 and an analogue-digital A/D converter 8, and is able to be positioned basically in contact with a layer of material (illustrated in FIG. 2) to measure its thickness.

In particular, the microwave sensor 6 includes a microwave transmitter and a microwave receiver (known and not illustrated for the sake of simplicity in the enclosed figures) to respectively send a signal onto the layer of material and to measure a response to the transmitted signal. In particular, the microwave sensor 6 includes a slot-type resonant circuit (not illustrated) characterized by a frequency response curve, basically centred around a resonance frequency, in correspondence of which there is a minimum amplitude value.

The microwave sensor 6 is a planar type sensor, whereby planar type sensor indicates a sensor which includes a slot-type resonant circuit connected to a planar transmission line by an electromagnetic coupling. Preferably, the resonant circuit is implemented by means of fractal or pseudo-fractal type geometric patterns.

Figure 2:
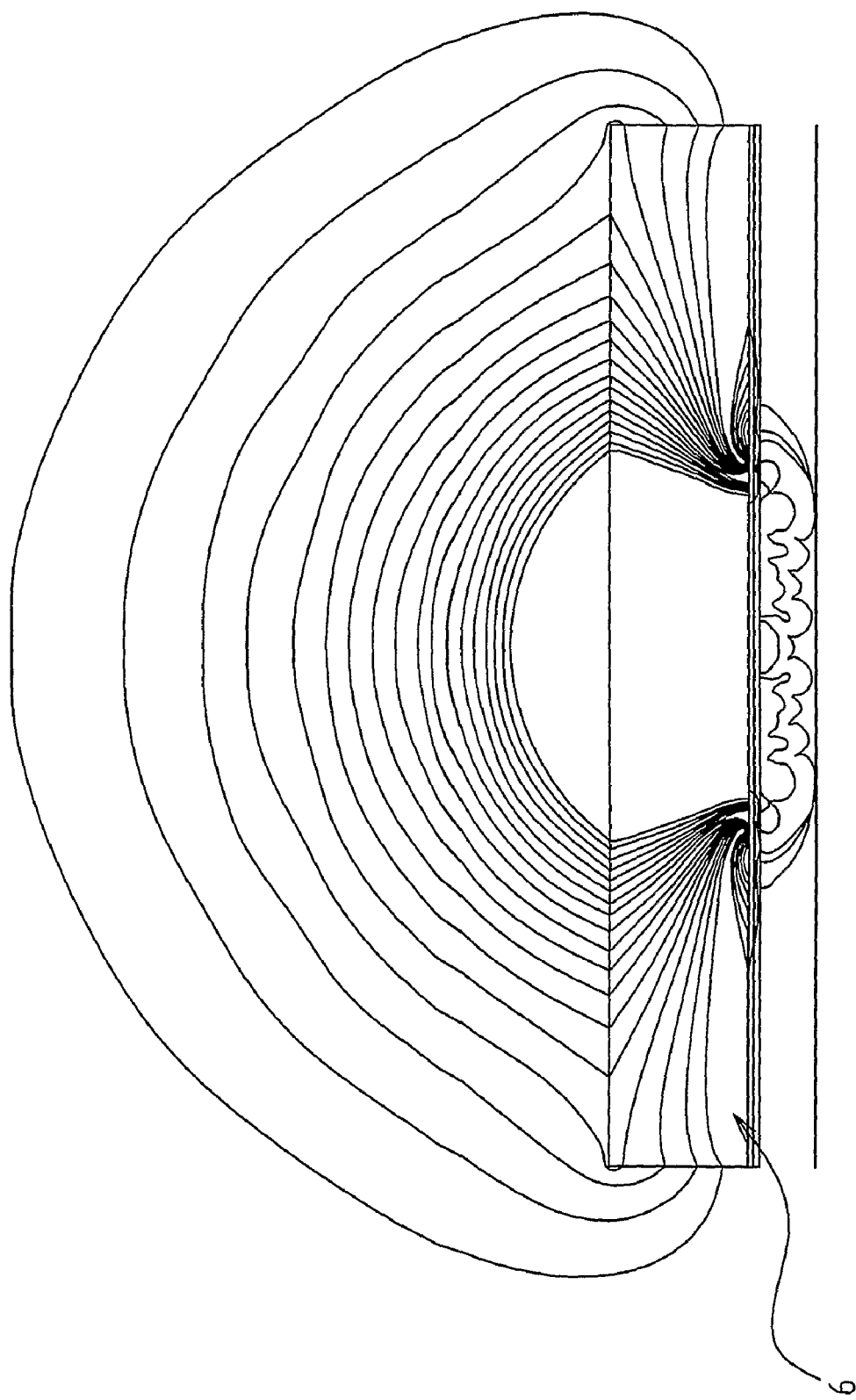
FIG. 2 shows a detail of the device of FIG. 1.

In particular, the sensor is generically flat and has a basically elliptic active emission zone that emits an electromagnetic field of well-defined shape; the component perpendicular to the sensor of the electromagnetic field is shown in FIG. 2.

The presence of a material in the proximity of the microwave sensor 6 alters the frequency response curve of the resonant circuit, in terms of a shift in the resonance frequency and therefore of a variation in the minimum amplitude, in a way that depends on the physical features of the material. The variation in the resonance frequency of the resonant circuit is basically related to the dielectric constant of the material analysed. Hence, for a specific dielectric constant, the variation in the resonance frequency is related to the thickness of the material and to other physical-chemical features related directly or indirectly to the dielectric constant.

With reference once again to FIG. 1, the temperature sensor 7 is of known type, and is able to measure temperature values, directly or indirectly, of the layer of material.

The A/D converter 8 is connected to the microwave sensor 6 and to the temperature sensor 7, and converts the analogue signals coming from such sensors into digital signals which are fed to the control unit 3. According to a preferred aspect of the invention, the A/D converter 8 is arranged in proximity of the microwave sensor 6.

The control unit 3 includes a control panel 10, a memory unit 13 and a processing unit 14.

The control panel 10 is generally provided with a display (not illustrated for reasons of simplicity in the enclosed figures) to visualize data relating to the current measurement and any statistics and trends over time relating to previous measurements.

The memory unit 13 is apt to store the data relating to the measurements performed by the reading head 2, in addition to calibration data of the microwave sensor 6 and/or of the temperature sensor 7.

The processing unit 14 is apt to process the data coming from the microwave sensor 6, from the temperature sensor 7 and from the memory unit 13 and is interfaceable with the outside, for example with other electronic control systems.

Figure 3:
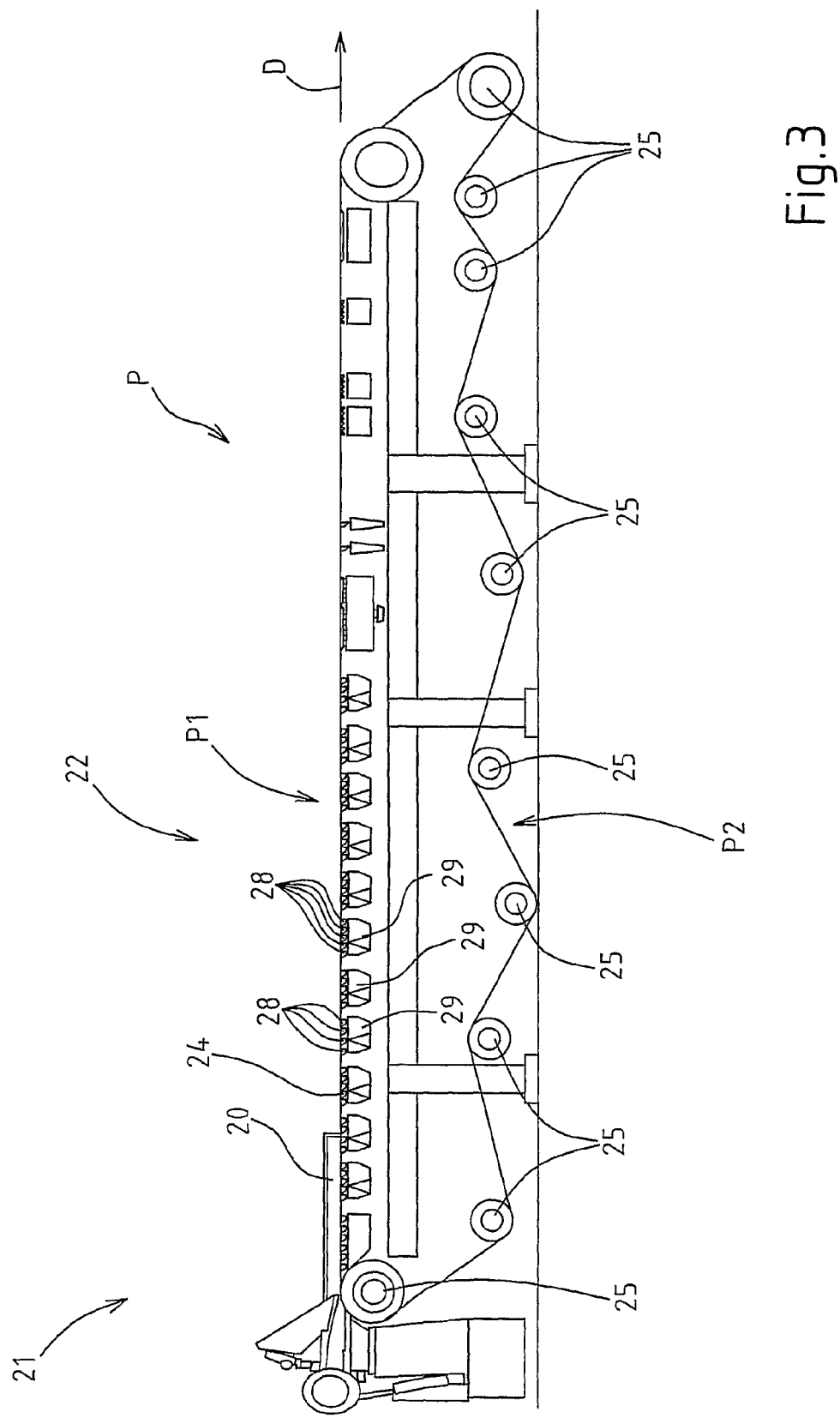
FIG. 3 shows a formation and drainage section of a paper making machine.
Figure 4:
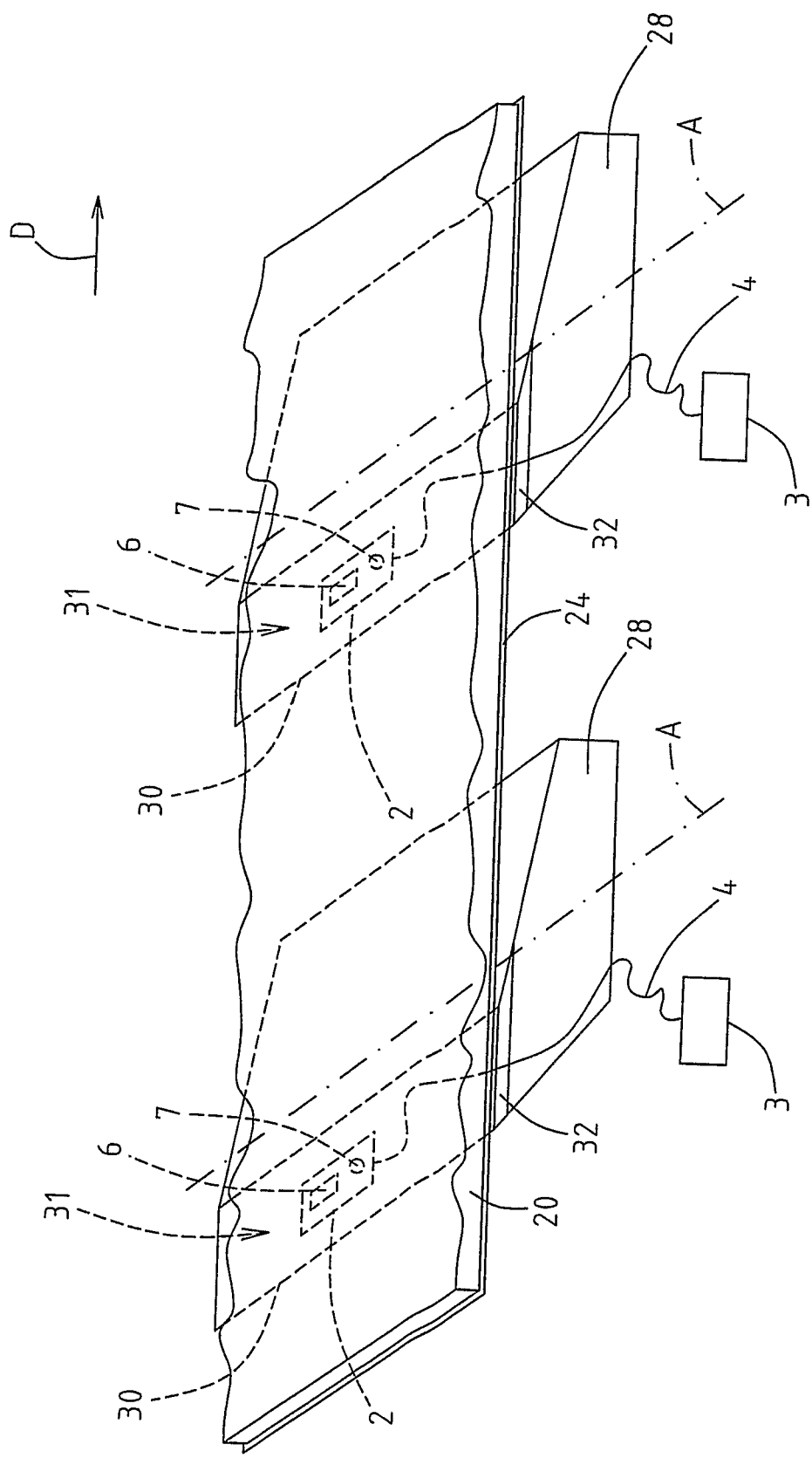
FIG. 4 is a perspective schematic diagram, with parts removed for reasons of clarity, of an embodiment of the device of FIG. 1.

In FIGS. 3 and 4, a preferred embodiment of the device 1 is illustrated, applicable to the field of the paper manufacturing industry.

In particular, the device 1 is used for measuring the thickness of a cellulosic pulp layer 20, composed of approximately 3% fibre and mineral additives and approximately 97% water.

In FIG. 3 a portion of a paper making machine 21 is illustrated, in particular a formation and drainage section 22 of the paper making machine 21, in which a forming fabric 24 is arranged and rotates in a loop along a path P. The path P is defined by an upper first portion P1, which extends substantially along a rectilinear and horizontal direction D, and by a lower second return portion P2, obtained by means of the passage of the forming fabric 24 between a plurality of cylinders 25. On an outer surface (the "straight") of the forming fabric 24, substantially along the first portion P1 of the path P, is arranged the cellulosic pulp layer 20 that is supported and transported by the forming fabric 24.

Under the forming fabric 24, substantially along the first portion P1 of the path P, and in contact with an inner surface (the "reverse") of the forming fabric 24, is arranged a plurality of substantially parallel blades 28, apt to remove from the cellulosic pulp layer 20 an aqueous layer which drains from the forming fabric 24. The water in the cellulosic pulp layer 20 tends, in fact, to pass through the fibres of the cellulosic pulp layer 20 and the forming fabric 24 and to generate an aqueous layer on the reverse of the forming fabric 24.

The blades 28 are divided into groups 29 spaced along the direction D, for example at a regular distance from one another. Inside each group 29, the blades 28 are spaced along the direction D and, for example, arranged at a regular distance from one another.

FIG. 4 shows only two blades 28 of a group 29, for reasons of simplicity. Each blade 28 extends substantially lengthwise along an axis A, substantially perpendicular to the direction D, for a length slightly greater than the width of the forming fabric 24 and is substantially wedge-shaped and characterized by the presence of a sharp edge 30 apt to mechanically remove the aqueous layer that drains from the reverse of the forming fabric 24.

Each blade 28 is arranged perpendicularly to the direction D of the first portion P1 of the path P below the forming fabric 24 with the sharp edge 30 in contact with the reverse of the forming fabric 24. In particular, the sharp edge 30 is carried by an end portion 31, preferably substantially flat, of the blade 28 that cooperates by contact, in use, with the reverse of the forming fabric 24.

The portion 31 is provided with a reading head 2 of the device 1 according to the present invention. In particular, the reading head 2 is integrated in the blade 28 so that the microwave sensor 6, preferably a planar type sensor, and the temperature sensor 7 of the reading head 2 are arranged superficially and facing the reverse of the forming fabric 24. In the non-limiting embodiment of FIG. 4, the reading head 2 is arranged on the surface of the portion 31 facing the reverse of the forming fabric 24 and is covered by a thin layer 32, preferably of ceramic material.

Each reading head 2, integrated in a respective blade 28, is connected to a respective control unit 3 by means of a connection cable 4, partially integrated in the blade 28.

According to a not illustrated variation, several reading heads 2, or all of the reading heads 2, of the blades 28 are connected to a control unit 3, which processes the data coming from the different reading heads 2 and visualizes such data on a single display.

Figure 5:
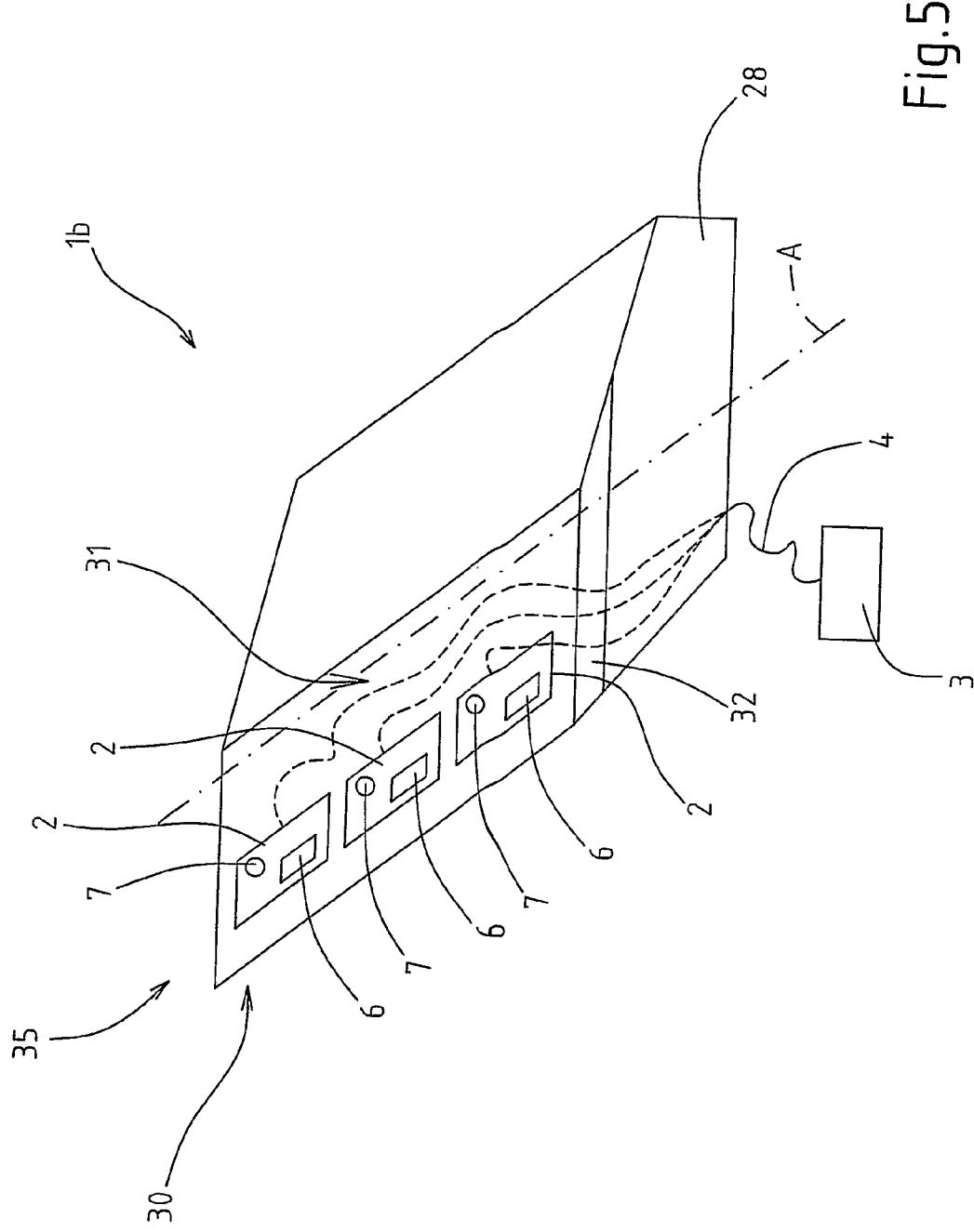
FIG. 5 is a perspective schematic diagram, with parts removed for reasons of clarity, of an alternative embodiment of the device of FIG. 1.

FIG. 5, in which the same parts, already shown previously, are indicated with the same reference numbers, shows a device 1b according to a different embodiment of the device of the invention, applied to a blade 28 which is wholly identical to those described previously. The device 1b includes an array 35 of reading heads 2 basically arranged in the portion 31 of a blade 28. The array 35 extends parallel to the axis A of the blade 28 and substantially for the entire length of the blade and may include a different number of reading heads 2, depending on the length of the blade 28 and the accuracy of the measurement required. In FIG. 5, purely by way of example, the array 35 includes three reading heads 2 alongside each other and parallel to the axis A. Also in this case, each reading head 2 includes a microwave sensor 6 and a temperature sensor 7.

In a variation not shown, the array includes a single temperature sensor and a variable number of reading heads, each of which includes a microwave sensor.

All the reading heads 2 of the same array 35 are connected to a control unit 3 by means of one or more connection cables 4.

According to a variation, not shown, all the reading heads 2 of the array 35 of several blades 28, or of all the blades 28, are connected to a control unit 3, that processes the data coming from the different reading heads 2 and visualizes them on a single display.

According to an additional variant, not illustrated in the figures enclosed, a part of the blades is provided with a device, including an array of reading heads, for each blade; and the remaining part of the blades, or some blades of the remaining part, is provided with a single reading head for each blade.

According to an further embodiment, the device 1, instead of being integrated in the paper making machine 21, is a portable device: the device 1 (as described previously with reference to FIGS. 1-2) includes, in this case, a portable reading head 2, that is dimensioned and shaped in such a way to be carried (manually by an operator or by means of a known service equipment) into the desired measurement position at the machine 21 and in proximity of the layer 20 of material to be measured, and specifically so that the microwave sensor 6 and the temperature sensor 7 are substantially in contact with the reverse of the forming fabric 24; also in this embodiment, the device 1 further includes a control unit 3 to process the data coming from the reading head 2 and to visualize the data on a display. The control unit 3 is, in turn, preferably portable, for example housed in a common casing together with the reading head 2, or is arranged in a remote position and connected, in a known manner, to the reading head 2.

In use, the microwave sensor 6 of each reading head 2 measures the frequency response of the cellulosic pulp layer 20 and the temperature sensor 7 indicates the temperature of the cellulosic pulp layer 20; the data relating to the frequency response and the temperature of the cellulosic pulp layer 20 are digitalized by the A/D converter 8 which processes them, according to known algorithms, in order to provide the thickness of the cellulosic pulp layer 20 and the quantity of water contained in the cellulosic pulp layer 20.

The control unit 3 is preferably connected to the control system (not illustrated in the enclosed figures) of the paper making machine 21 to transmit the measured data. In this manner, the control system of the machine 21 is able to respond to any abnormalities of the drainage stage of the formation and drainage section 22. For example, if a microwave sensor 6 of an array 35 detects excessive water content in the portion of cellulosic pulp layer 20 which it is facing, it sends a signal to the control system of the machine 21, which will then reduce the quantity of water in the identified portion.

The present invention presents the following advantages.

Above all, the use of a microwave planar type sensor in the device of the invention allows the attainment of the generation of a more uniform microwave field, with increased penetration capacity compared to that attainable with conventional microwave sensors. In particular, the electromagnetic field of the planar type sensor of the device, according to the present invention, is definable both in terms of its shape and its behaviour thanks to the fact that the slot-type resonant circuit is implemented by means of fractal or pseudo-fractal type geometric patterns.

Secondly, the microwave planar type sensors are advantageously less sensitive to variations in temperature compared to conventional microwave sensors, since in microwave planar type sensors the resonance chamber is of reduced size and is less affected by thermal expansion or contraction.

In addition, the almost direct coupling between the microwave sensor and the analogue-digital converter allows the attainment of greater accuracy of measurement. In fact, the lines that conduct the analogue signal from the sensor to the converter are very short and therefore less prone to specific problems caused by electromagnetic fields outside the device. This last aspect, combined with the reduced size of the microwave planar type sensors (up to approximately 50% smaller than conventional microwave sensors), allows the broadening of the fields of application of the device, according to the present invention. For example the microwave planar type sensor is integrable in the blades of a machine suitable for manufacturing paper, which are able to remove water from the formation wire during the passage through the formation and drainage section. By means of such device it is therefore possible to uniformly evaluate the quantity of water present in the cellulosic pulp suspension and therefore to evaluate the uniformness of the sheet of paper that is being formed. In particular, the presence of an array of reading heads allows the transversal "scanning" of the cellulosic pulp suspension that allows the attainment of important information concerning the quality of the drainage.

Lastly, it is clear that variations and/or modifications may be made to the device and the machine described herein, without so departing from the scope of the enclosed claims.

The invention claimed is:

1. A paper making machine comprising:
   a forming fabric that rotates in a loop along a path to transport a cellulosic pulp layer;
   a plurality of blades, each of which extends along an axis and is provided with a sharp edge to remove an aqueous layer of the cellulosic pulp layer that drains from the forming fabric; and
   at least one device for measuring the thickness of the cellulosic pulp layer, the at least one device comprising a reading means which includes a microwave sensor, and a control means connected to the reading means,
   wherein the reading means is disposed on at least one blade in the plurality of blades.

2. A machine according to claim 1, characterized in that the microwave sensor is a microwave planar type sensor.

3. A machine according to claim 1, characterized in that the reading means is arranged in a portion of the blade including the sharp edge, which cooperates by contact, in use, with the forming fabric.

4. A machine according to claim 3, characterized in that the reading means includes at least one reading head including a microwave sensor.

5. A machine according to claim 4, characterized in that the reading head is arranged in the portion of the blade in such a way that the microwave sensor is positioned superficially and facing the forming fabric.

6. A machine according to claim 5, characterized in that the reading means includes an array of reading heads.

7. A machine according to claim 6, characterized in that the reading heads of the array are arranged in the portion of the blade and parallel to the axis of the blade.

8. A machine according to claim 4, characterized in that the control means includes a plurality of control units; each reading head being connected to a respective control unit.

9. A machine according to claim 4, characterized in that the control means includes a control unit; all the reading heads being connected to the control unit.

10. A machine according to claim 4, characterized in that the control means includes a plurality of control units; the reading heads of one or more arrays being connected to a respective control unit.

11. A machine according to claim 1, characterized in that the control means of the device is designed to calculate and store the thickness of a cellulosic pulp layer.

12. A paper making machine comprising:
- a forming fabric that rotates in a loop along a path to transport a cellulosic pulp layer;
- a plurality of blades, each of which extends along an axis and is provided with a sharp edge to remove an aqueous layer of the cellulosic pulp layer that drains from the forming fabric; and
- at least one device for measuring the thickness of the cellulosic pulp layer, the at least one device comprising a reading means and a control means connected to the reading means,
- wherein the reading means is disposed on at least one blade in the plurality of blades.

* * * * *